(12) United States Patent
Woerlein et al.

(10) Patent No.: US 8,750,965 B2
(45) Date of Patent: Jun. 10, 2014

(54) TRACKING RIGID BODY STRUCTURES WITHOUT DETECTING REFERENCE POINTS

(75) Inventors: Swen Woerlein, Munich (DE); Jens Witte, Munich (DE); Nils Frielinghaus, Heimstetten (DE)

(73) Assignee: Brainlab AG, Feldkirchen (DE)

( * ) Notice: Subject to any disclaimer, the term of this patent is extended or adjusted under 35 U.S.C. 154(b) by 2276 days.

(21) Appl. No.: 11/747,466

(22) Filed: May 11, 2007

(65) Prior Publication Data

US 2007/0274589 A1 Nov. 29, 2007

Related U.S. Application Data

(60) Provisional application No. 60/821,303, filed on Aug. 3, 2006.

(30) Foreign Application Priority Data

May 11, 2007 (EP) .................................... 06009745

(51) Int. Cl.
*A61B 5/05* (2006.01)

(52) U.S. Cl.
USPC ......................................................... 600/424

(58) Field of Classification Search
USPC .................................................. 600/414, 426
See application file for complete search history.

(56) References Cited

U.S. PATENT DOCUMENTS

| | | | |
|---|---|---|---|
| 6,205,411 B1 | 3/2001 | DiGioia, III et al. | |
| 6,236,875 B1 | 5/2001 | Bucholz et al. | |
| 6,719,757 B2 * | 4/2004 | Neubauer et al. | 606/53 |

FOREIGN PATENT DOCUMENTS

| | | |
|---|---|---|
| DE | 43 04 570 | 8/1994 |
| DE | 101 35 156 | 2/2003 |
| WO | 99/21498 | 5/1999 |

OTHER PUBLICATIONS

Labadie et al. Image-guided otologic surgery. International Congress Series. 1256:627-632. 2003.*

* cited by examiner

*Primary Examiner* — Parikha Mehta
(74) *Attorney, Agent, or Firm* — Tucker Ellis LLP

(57) ABSTRACT

A method for tracking at least one rigid object part of a rigid reference object, wherein the rigid object part can be detached or removed from the rigid reference object is provided. The method includes obtaining a patient data set of a region around the object part, attaching a first reference star in a fixed position relative to the object part situated on the reference object, detecting reference points on the reference object and ascertaining three-dimensional spatial positions of the reference points of the reference object, assigning the three-dimensional spatial positions of the reference points of the reference object to corresponding points in the patient data set, attaching a second reference star to the object part, ascertaining positional information of the second reference star; and ascertaining positional information of the object part or tracking the object part based on the positional information of the second reference star.

21 Claims, 2 Drawing Sheets

TRACKING RIGID BODY STRUCTURES WITHOUT DETECTING REFERENCE POINTS

RELATED APPLICATION DATA

This application claims priority of U.S. Provisional Application No. 60/821,303 filed on Aug. 3, 2006, which is incorporated herein by reference in its entirety.

FIELD OF THE INVENTION

The present invention relates to tracking at least one rigid object part, such as a rigid body or bone structure of a patient. More particularly, the invention relates to an apparatus and method for tracking a rigid object part, wherein the rigid object part may be detached or removed from a rigid reference object, such as a rigid body or bone structure of the patient, and tracked and displayed in a patient data set (e.g., a CT recording) without reference points on the object part being detected by a medical navigation system. The present invention further relates to a method and apparatus for offsetting, repositioning or exchanging the rigid object part in the reference object to a predetermined position, wherein the rigid object part can be placed onto the predetermined position by tracking or determining the position of the rigid object part.

BACKGROUND OF THE INVENTION

Conventionally, bone structures are registered within a medical navigation system or the like to enable said bone structures to be tracked within a medical workspace. More specifically, points on body parts to be tracked are detected and their positions ascertained, thereby enabling the body part to be registered and tracked.

U.S. Pat. No. 6,236,875 relates to systems that generate and use images recorded between medical and surgical operations. The images are helpful when performing the operations, and show the relative position of various body parts and instruments.

SUMMARY OF THE INVENTION

The present invention enables small, rigid object parts or bone structure parts that are difficult or impossible to register to be quickly and easily tracked or repositioned. A "rigid object" refers to a body structure, and a "rigid object part" refers to a part of a body structure that does not change its shape between recording the body or body structure part and a medical procedure or operation, and is not compressed or deformed.

In a method for tracking at least one rigid object part, in particular a rigid body or bone structure part of a patient, the object part, which can be detached or removed from a rigid reference object, in particular a rigid body or bone structure of the patient, can be tracked by means of an image-assisted navigation system, an image-guided surgery (IGS) system or a tracking system (hereinafter referred to as a navigation system).

A patient data set, such as a computer tomography (CT) data set or other medical data set of the patient in which rigid body or bone structures of a patient can be shown, is then provided or ascertained. The patient data set may be a previously recorded patient data set, such as for example a patient data set ascertained by means of a computer tomograph, or the patient data set can be ascertained, for example by means of a computer tomograph or other medical imaging system, before, during or between individual steps of the method for tracking the rigid object part. The patient data set can be a data set, in particular at least one recording, of a region around the object part, body or bone structure part or around at least a part of the object, reference object, the rigid body or bone structure.

The object part or bone structure part, which may be detachably or removably connected to the object or reference object, or which may be detachably or removably arranged on the object or reference object, can be marked in the patient data set. The object part can be marked, for example, by being drawn in or selected by a physician in a representation of the patient data set, and can be highlighted or colored in the patient data set. The marked object part or parts also can be semi-automatically or automatically marked and segmented. The object part also can be marked in the patient data set by placing resection lines thereon. By marking the object part (e.g., by highlighting the object part in the patient data set, or by segmenting the object part in the patient data set), the object part can be moved or shifted in a representation of the patient data set relative to the rest of the patient data set or to the reference object.

A cranial bone structure (e.g., a cranial bone) of the patient is preferably used as the reference object, and a bone of the cranial bone structure or of the cranial bone, such as the frontal bone, the zygomatic bone, the maxilla, the intermaxilla, the mandible, the nasal bone, the lacrimal bone, the palatine bone, the vomer or the hyoid is preferably used as the object part for tracking the respective bone structure part during, for example, an oral-surgical operation or to ascertain and show its position. It is also possible to use an arm bone structure or leg bone structure as the reference object, and a bone structure part that can be detached or removed from arm bone structure or leg bone structure as the object part.

A first reference star may be arranged on or attached to the reference object at an arbitrary or predetermined position. The position of the first reference star may be situated on the reference object or on a part or object part connected to the reference object. Further, the first reference star may be in a fixed distance relationship to the at least one object part that is marked or to be tracked, and not situated on the object part that is marked or to be tracked. The position of the first reference star can be detected or ascertained by means of the navigation system, can be predetermined by the navigation system or known to the navigation system.

Reference points on the reference object may be detected by means of physical contact, or without physical contact (e.g., by means of a laser pointer). Detection of the reference points may be transmitted wirelessly or via a wire connection to the navigation system, such that by taking into account the position of the first reference star detected by the navigation system or known to the navigation system, three-dimensional spatial positions with respect to a reference coordinate system or global coordinate system can be assigned to the detected reference points, such as the first reference star. A plurality of reference points can be detected and used to register the reference object with respect to the first reference star or with respect to the reference coordinate system.

The ascertained three-dimensional spatial positions of the reference points of the reference object can be assigned to the corresponding points or locations or positions in the patient data set by means of the navigation system. A part of the object or the object, therefore, can be registered with respect to the ascertained or provided patient data set, wherein a region around the object part to be tracked can be registered. The points on the object or bone structure, or the surface of the object or bone structure, therefore can be assigned almost one-to-one to the patient data set, such that changes in the object, shifts in the object or shifts in object parts relative to the object can be shown in the patient data set, such as the recordings of the object.

A second reference star can be arranged on the object part to be tracked, before the object part is detached or removed from the object, wherein the distance or distance relationship between the second reference star and the first reference star can be predetermined or can be ascertained by the navigation system. The distance between the second reference star arranged on the object part and the first reference star arranged on the object therefore is known to the navigation system. Thus, the spatial position of the second reference star with respect to the reference or global coordinate system, such as the first reference star, is known to or can be determined by the navigation system.

The shape and/or size of the object part or bone structure part also can be known to the navigation system (e.g., by defining resection lines) or can be determined by the navigation system. The object part or bone structure part can also exhibit a fixed distance from the object, or a constant distance relationship to the object before the object part is detached. By taking into account the distance relationship or the position of the first reference star relative to the second reference star and/or by taking into account the shape and/or size of the object part, it is possible to deduce the position of the object part relative to the reference coordinate system, such as the first reference star. This enables the object part or bone structure part to be registered with respect to the patient data set, and changes in position or shifts in the object part relative to the object can be shown in the patient data set.

If the object part or bone structure part is detached or removed from the object or bone structure and moved in space, then the navigation system can ascertain the position or positional information of the second reference star arranged on the object part and, thus, the position or positional information of the object part or bone structure part. Two-dimensional and/or three-dimensional images of the object part, distance characteristics or distances between the object part and parts of the object, structures of the object, directions or movement directions of the object part and/or orientations of the object part relative to the object can be ascertained as positional information of the object part and shown in the patient data set, such as the recordings of the object. The movement trajectory of the object part can be two-dimensionally or three-dimensionally shown in the patient data set or in the patient recordings, by means of the segmented object part. Distances or coordinates of the object part in space or with respect to the object, the surface of the object or the structure of the object also can be ascertained and shown.

In accordance with another aspect of the invention, there is provided a method for offsetting, repositioning or exchanging the object part in the reference object to a predetermined position, wherein the method for tracking the object part and for ascertaining, showing and/or outputting positional information of the object part can be used for precisely placing or offsetting the object part.

In the ascertained or provided patient data set of the region around the object part, of the entire object, or of a part of the object, the object part marked in the patient data set may be offset relative to the predetermined or selected position, for example by means of a planning software, such that the marked or segmented object part is placed or repositioned in the patient data set of the object and, for example, highlighted in color.

If the object part or bone structure part is detached or removed from the object or bone structure and, for example, changed or exchanged for a new object part, it can be offset to or placed onto the predetermined position based on the positional information of the object part ascertained by means of the navigation system. The exchanged or changed object part or the unchanged object part can be shown in the patient data set and moved until it has reached the predetermined position in the patient data set and in the actual object. The representation of the object part and of the object in the patient data set preferably serves to precisely locate the predetermined position in the actual object. Directions or orientations also can be specified or shown that specify how the object part has to be moved in order to reach the predetermined position. By taking into account the positional information of the object part, it is possible to position or reposition the object part at the predetermined position.

Once the object part has been fixed or connected to the reference object at the desired or predetermined position, the second reference star can be removed from the object part and the first reference star can be removed from the object.

The methods described herein may be embodied as a computer program which, when it is loaded onto a computer or is running on a computer, performs the described methods. Further, the computer program may be embodied on a computer readable medium.

A device for tracking and offsetting at least one rigid object part, such as a rigid body or bone structure part of a patient, includes an image-assisted navigation system or IGS (image-guided surgery) system and a display device such as a screen or monitor which can also be integrated into the navigation system. The object part or bone structure part is detachably or removably situated on a rigid reference object, such as a rigid body or bone structure, of the patient. A known or stored patient data set, such as a CT data set of a patient, can be input into the device, for example, via an input device. Alternatively, the device can include a medical imaging system such as a computer tomograph (CT) as the input device, by means of which the device can ascertain a patient data set, such as a plurality of computer tomography recordings of the object or of a part of the object or of a region around the object part. The input or ascertained patient data set can be displayed or shown on the display device, which may be coupled to the IGS system or navigation system via a wireless or wired connection. The object part or bone structure part can be marked in the displayed or shown patient data set, for example, by selecting the object part or bone structure part on the display device (e.g., via a touch screen) or by inputting or selecting the name or the coordinates or other information designating the object part or bone structure part.

If a first reference star is arranged on the reference object in a fixed distance relationship to the object part, the navigation system can ascertain three-dimensional spatial positions of reference points of the reference object via contact or contactless means. The three-dimensional spatial positions of the reference points can be defined with respect to a reference or global coordinate system, the origin of which may lie in the first reference star. If the three-dimensional spatial positions of the reference points of the reference object are known to the navigation system, the spatial positions can be assigned to the corresponding points or locations in the patient data set, or the reference object can be registered with the patient data set displayed in the display device. This enables changes or shifts in the object or movements relative to the object in the patient data set to be displayed on the display device.

If a second reference star is arranged on the object part, then the image-assisted navigation system can ascertain the position of the second reference star relative to the first reference star, such that the position of the second reference star or of the object part relative to a reference or global coordinate system can be ascertained by the navigation system. Based on the ascertained position of the second reference star in the reference coordinate system and on the shape and/or size of the object part or bone structure part, the navigation system can deduce the spatial position of the object part relative to the reference coordinate system, such that the object part can be registered with respect to the reference coordinate system. The object part can be registered without points on the object part being detected with respect to the patient data set, such that movements or shifts in the object part relative to the object can be shown on the display device on the basis of the patient data set.

If the object part or bone structure part is removed from the object, the navigation system can spatially ascertain or track the position or movement of the object part and can show the position or movement or positional information of the object part in the patient data set on the display device. Two-dimensional or three-dimensional images of the movement trajectory or of the movement of the object part can be shown on the display device, or coordinates or directions can be specified in which the object part is moved or is to be moved. This can ensure that the object part is precisely positioned at the predetermined desired position. The object part also can be moved and the movement trajectory tracked and shown on the display device. The object part also can be changed or exchanged, for example, by a medical operation, and tracked in the patient data set on the display device such that the object part can be inserted at the original position or at a predetermined or desired new position.

The device also can include a positioning system that can automatically attach the first and second reference star to the object and/or object part or arrange the first and second reference star on the object and/or object part and/or remove the first and second reference star from the object and/or object part.

BRIEF DESCRIPTION OF THE DRAWINGS

The forgoing and other features of the invention are hereinafter discussed with reference to the drawings.

DETAILED DESCRIPTION

Figure 1A:
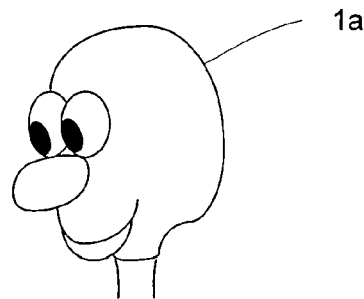
FIGS. 1a to 1g are schematic diagrams showing the sequence of an exemplary method for tracking a temporal bone of a patient in accordance with the invention.
Figure 1B:
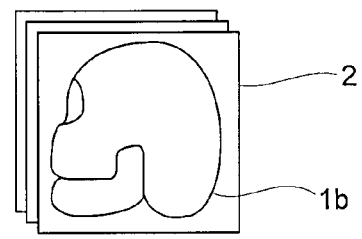
Figure 1C:
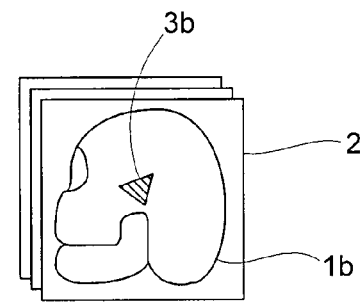
Figure 1D:
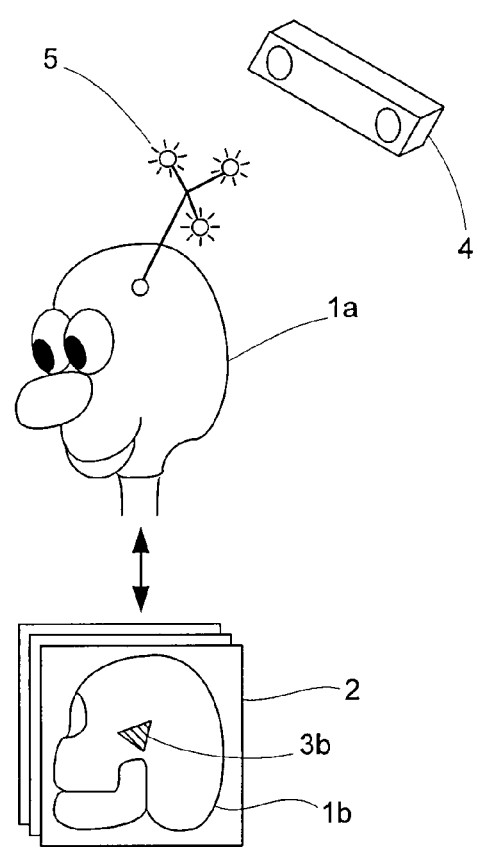

FIGS. 1a to 1g show an exemplary sequence of a method for tracking a rigid object part. FIG. 1a shows the head 1a of a patient, wherein computer tomography (CT) recordings of the patient head 1a are to be (or have been) obtained. The recordings include image data for the cranial bone 1b of the patient in a patient data set 2 (e.g., CT recordings or the like) as shown in FIG. 1b. In the patient data set, a bone 3b that is to be tracked or replaced (e.g., the temporal bone) is defined and marked. The bone 3b also may be segmented from the patient data set 2, as shown in FIG. 1c. If a first reference star 5 is attached to the head 1a of the patient, as shown in FIG. 1d, the position of the first reference star 5 can be detected by a navigation system 4 (e.g., an optical navigation system) and the three-dimensional spatial position of the first reference star 5 can be defined with respect to a reference coordinate system, such as the origin of the first reference star 5. By detecting reference points on the head 1a of the patient, the reference points can be assigned to the corresponding points in the CT images 2, such that the head 1a or cranial bone 1b of the patient can be registered with respect to the CT images 2 of the cranial bone 1b.

Figure 1E:
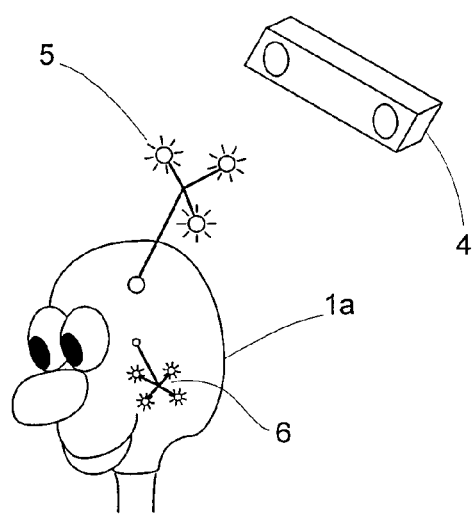
Figure 1F:
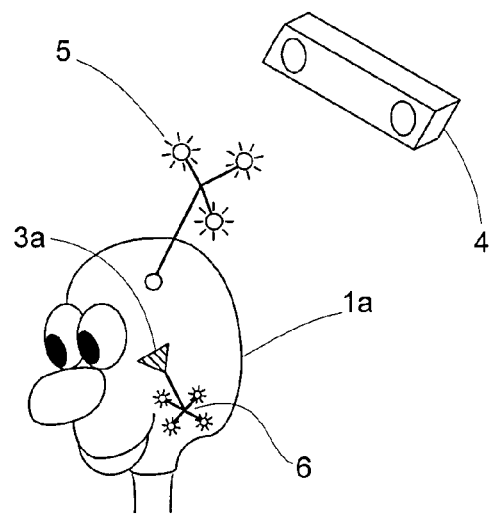
Figure 1G:
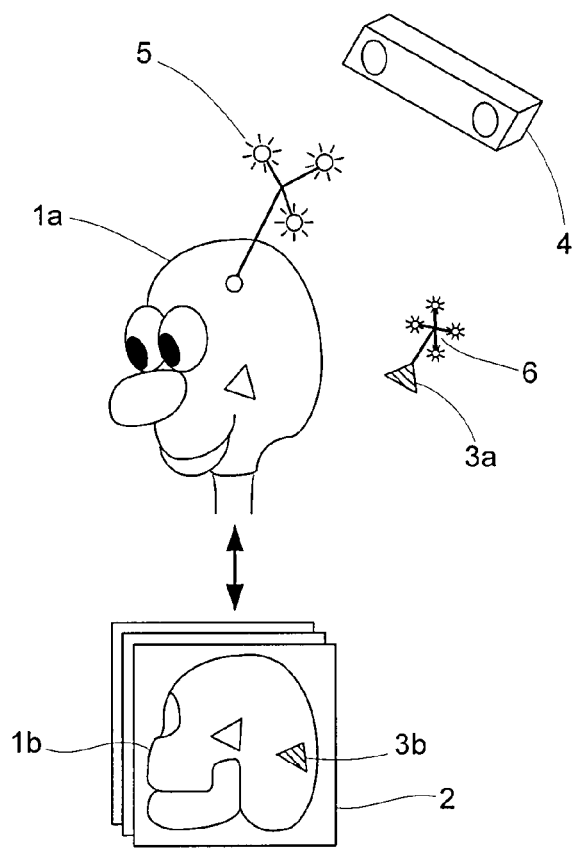

If a second reference star 6 is arranged on the temporal bone 3a, as shown in FIG. 1e, then the position of the second reference star 6 and the position of the temporal bone 3a can be spatially ascertained by the navigation system 4 (see FIGS. 1e and 1f). If the temporal bone 3a is removed or detached from the cranial bone 1a, the navigation system 4 can spatially ascertain the three-dimensional position of the temporal bone 3a by means of the second reference star 6. Further, the navigation system 4 can show the movement trajectory or the position of the temporal bone 3b in the CT images 2 on a display device, as shown in FIG. 1g. The temporal bone 3a thus can be spatially tracked or the position of the temporal bone 3a can be ascertained and shown in the CT images 2, without reference points on the temporal bone 3a being detected and without the reference points of the temporal bone 3a being assigned to corresponding points in the patient data set 2. The temporal bone 3a also can be changed or exchanged, for example, by a medical operation, or a replacement (e.g., an implant) of the temporal bone 3a can be produced and inserted at the marked starting position or at a new predetermined or desired marked location in the patient data set 2.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for tracking at least one rigid object part of a rigid object, wherein the rigid object part is detachable or removable from the rigid object, comprising:

obtaining a patient data set of a region around the rigid object part;

attaching a first reference device in a fixed position relative to the rigid object part situated on the rigid object;

detecting reference points on the rigid object and ascertaining three-dimensional spatial positions of the reference points on the rigid object;

assigning the three-dimensional spatial positions of the reference points of the rigid object to corresponding points in the patient data set;

attaching a second reference device to the rigid object part;

ascertaining positional information of the second reference device; and ascertaining positional information of the rigid object part or tracking the rigid object part based on the positional information of the second reference device.

2. The method according to claim 1, wherein the rigid object part is a rigid body or bone structure part of a patient, and the rigid object is a rigid body or bone structure of the patient.

3. The method according to claim 1, wherein obtaining a patient data set includes obtaining a computer tomography (CT) data set.

4. The method according to claim 1, where assigning the three-dimensional spatial positions of the reference points includes using an image-assisted navigation system or an IGS (image-guided surgery) system to assign the positions of the reference points.

5. The method according to claim 4, wherein ascertaining positional information of the second reference device includes using the image-assisted navigation system or the IGS system to ascertain the positional information.

6. The method according to claim 4, wherein ascertaining positional information of the rigid object part or tracking the rigid object part includes using the image-assisted navigation system or the IGS system to ascertain the positional information.

7. A method for offsetting, repositioning or exchanging rigid object part in a rigid object to a predetermined position, comprising:
marking the rigid object part in the patient data set;
tracking the rigid object part according to claim 1;
positioning a copy of the marked object part in the patient data set at the predetermined position;
offsetting the rigid object part in the rigid object to the predetermined position based on the ascertained positional information of the rigid object part; and
fixing the rigid object part to the reference object.

8. The method according to claim 7, further comprising arranging the rigid object part in a fixed and known distance relationship to the rigid object.

9. The method according to claim 1, further comprising ascertaining a distance relationship between the first and second reference device.

10. The method according to claim 1, further comprising automatically or semiautomatically identifying the rigid object part in the patient data set by drawing in or placing resection lines in the patient data set.

11. The method according to claim 1, further comprising ascertaining a shape and/or size of the rigid object part.

12. The method according to claim 1, wherein ascertaining positional information of the rigid object part includes ascertaining two-dimensional and/or three-dimensional images, distance characteristics, directions and/or orientations as positional information of the rigid object part.

13. The method according to claim 1, further comprising using a cranial bone structure, an arm bone structure or a leg bone structure as the rigid object, and using a bone of the respective bone structure, a zygomatic bone, a maxilla, an intermaxilla, a mandible, a nasal bone, a lacrimal bone, a palatine bone, a vomer or a hyoid is used as the rigid object part.

14. A computer program embodied on a non-transitory computer readable storage medium for tracking at least one rigid object part of a rigid object, wherein the rigid object part is detachable or removable from the rigid object, wherein a first reference device is attached in a fixed position relative to the rigid object part situated on the rigid object, and a second reference device is attached to the rigid object part, comprising:
code that obtains a patient data set of a region around the rigid object part;
code that detects reference points on the rigid object and ascertains three-dimensional spatial positions of the reference points on the rigid object;
code that assigns the three-dimensional spatial positions of the reference points of the rigid object to corresponding points in the patient data set;
code that ascertains positional information of the second reference device; and
code that ascertains positional information of the rigid object part or tracks the rigid object part based on the positional information of the second reference device.

15. A device for tracking and/or offsetting at least one rigid object part of a rigid object of a patient, wherein the rigid object part is detachable or removable from a rigid object, comprising:
an image-assisted navigation system configured to
detect reference points on the rigid object on which a first reference device is situated, said reference device arranged in a fixed position relative to the rigid object part,
ascertain three-dimensional spatial positions of the reference points of the reference object from the detected reference points on the rigid object,
assign the three-dimensional spatial positions of the reference points of the rigid object to corresponding points in the patient data set, and
ascertain positional information of the rigid object part or track the rigid object part based on positional information of a second reference device arranged on the rigid object part; and
a display device operatively coupled to the image-assisted navigation system for displaying the patient data set and the positional information of the rigid object part.

16. The device according to claim 15, comprising an input device operatively coupled to the image-assisted navigation system or an image guided surgery (IGS) system, said input device operative to accept the patient data set.

17. The device according to claim 16, wherein the input device is a medical imaging system operative to ascertain the patient data set.

18. The device according to claim 15, further comprising a positioning system for attaching the first reference device to the rigid object or arranging the first reference device on the rigid object and for attaching the second reference device to the rigid object part or arranging the second reference device on the rigid object part.

19. The device according to claim 15, wherein the image-assisted navigation system is configured to ascertain the positional information of the rigid object part without detecting reference points on the rigid object part.

20. The method according to claim 1, wherein ascertaining the positional information of the rigid object part includes ascertaining the positional information of the rigid object part without detecting reference points on the rigid object part.

21. The method according to claim 1, further comprising registering the rigid object part with respect to the patient data set.

* * * * *